United States Patent
Rao et al.

(10) Patent No.: US 8,324,381 B2
(45) Date of Patent: Dec. 4, 2012

(54) PREPARATION OF ESTER OF PURINE DERIVATIVES

(75) Inventors: Dharmaraj Ramachandra Rao, Thane (IN); Rajendra Narayanrao Kankan, Mumbai (IN); Vidyadhar Purushottam Pande, Kalyan (IN)

(73) Assignee: CIPLA Limited, Mumbai (IN)

( * ) Notice: Subject to any disclaimer, the term of this patent is extended or adjusted under 35 U.S.C. 154(b) by 476 days.

(21) Appl. No.: 11/725,681

(22) Filed: Mar. 20, 2007

(65) Prior Publication Data

US 2007/0225305 A1    Sep. 27, 2007

(30) Foreign Application Priority Data

Mar. 21, 2006    (IN) .............................. 394/MUM/2006

(51) Int. Cl.
    *C07D 473/18*    (2006.01)
(52) U.S. Cl. ....................................................... 544/276
(58) Field of Classification Search .................. None
    See application file for complete search history.

(56) References Cited

U.S. PATENT DOCUMENTS

| | | | | |
|---|---|---|---|---|
| 5,543,414 A * | 8/1996 | Nestor et al. | ................... | 544/276 |
| 5,700,936 A * | 12/1997 | Arzeno | .......................... | 544/276 |
| 5,869,493 A * | 2/1999 | Engelhardt et al. | ........... | 544/276 |
| 6,083,953 A * | 7/2000 | Nestor et al. | ................... | 544/276 |
| 6,103,901 A * | 8/2000 | Arzeno et al. | ................. | 544/276 |
| 2002/0042424 A1* | 4/2002 | Nestor et al. | ................... | 514/262 |
| 2008/0076923 A1* | 3/2008 | Belogi et al. | .................. | 544/276 |
| 2011/0207931 A1* | 8/2011 | Katkam et al. | ................. | 544/276 |

FOREIGN PATENT DOCUMENTS

| | | | |
|---|---|---|---|
| EP | 694547 A2 | * | 1/1996 |
| WO | WO 9727197 A1 | * | 7/1997 |
| WO | WO 9727198 A1 | * | 7/1997 |
| WO | WO 9821223 A1 | * | 5/1998 |

* cited by examiner

*Primary Examiner* — Mark Berch
(74) *Attorney, Agent, or Firm* — Conley Rose, P.C.; Rodney B. Carroll

(57) ABSTRACT

A process for the preparation of valganciclovir with triacetyl ganciclovir (V) as a starting material, comprising the following steps: selective hydrolysis, reacting with a coupling agent and CBZ valine and a solvent, followed by hydrolysis under basic conditions and hydrogenolysis in the presence of a catalyst.

7 Claims, No Drawings

PREPARATION OF ESTER OF PURINE DERIVATIVES

FIELD OF INVENTION

This invention relates to the preparation of amino acid ester of purine derivatives or pharmaceutically acceptable salts thereof.

More specifically, the invention relates to the L-monovaline ester derived from 2-(2-amino-1,6-dihydro-6-oxo-purin-9-yl)methoxy-1,3-propane-diol and its pharmaceutically acceptable salts.

DEFINITIONS

As used in the present specification, the following words and phrases are generally intended to have the meanings as set forth below, except to the extent that the context in which they are used indicates otherwise.

CBZ means "Benzyloxycarbonyl"

DCC means "N,N-dicylohexyl carbodiimide."

CDI means N,N-Carbonyl diimidazole

"Derivative" is a compound obtainable from the original compound by at least one chemical process.

DMF means "N,N-dimethyl formamide".

"Esterification" means a chemical reaction resulting in the formation of at least one ester product.

"Hydrogenolysis" means the breaking of a chemical bond in an organic molecule with the simultaneous addition of a hydrogen atom to each of the resulting molecular fragments.

"Selective hydrolysis" in the context of this invention means the content of the desired hydrolysed product is greater than 50%.

"Protecting group" means a chemical group that (a) preserves a reactive group from participating in an undesirable chemical reaction; and (b) can be easily removed after protection of the reactive group is no longer required. For example, the benzyl group is a protecting group for a primary hydroxyl function.

"Purine" means a nitrogenous base found in nucleotide, it consists of a pyrimidine ring and an imidazole ring fused together. Guanine is a purine derivative.

DESCRIPTION OF THE BACKGROUND & PRIOR ART

Valganciclovir is a mono-L-valyl ester prodrug of the antiviral compound ganciclovir.

Valganciclovir is represented by chemical formula I, wherein Z is, hydrogen, is chemically, a L-valyl ester of 2-(2-amino-1,6-dihydro-6-oxo-purine-9-yl)-methoxy-3-hydroxy-1-propane.

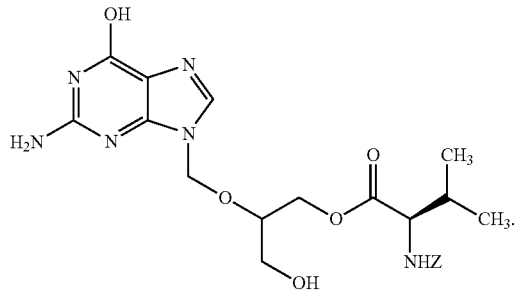

Formula I

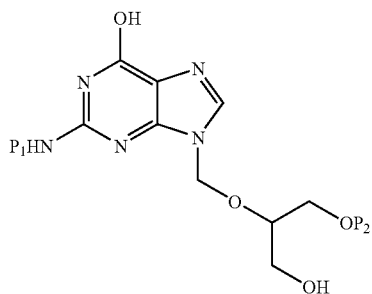

Formula II

Ganciclovir of Formula II, where $P_1$ and $P_2$ are hydrogen, is disclosed in U.S. Pat. No. 4,355,032.

Ganciclovir inhibits replication of human cytomegalovirus both in vitro and in vivo. When administered orally, Ganciclovir has a very low rate of absorption. Ganciclovir is mostly used as an intravenous infusion.

Antiviral Purine derivatives with an acyclic chain in the 9 position, such as acyclovir (INN name) & Ganciclovir (INN name) have been disclosed in British Patent 1523865 & U.S. Pat. No. 4,355,032 respectively.

Antiviral compounds with better water solubility as compared to ganciclovir have been disclosed in British Patent Application GB 2 122 618, without mention of mono- or bis L-valyl esters of ganciclovir.

Though Bis-L-valyl ester prodrug of ganciclovir with a better bioavailability profile is mentioned in European Patent Application 0 375 329, it does not disclose any details as to utility or preparation for mono L-valyl ester of ganciclovir.

Mono- and diacyl esters of ganciclovir are disclosed by John C. Martin et al. in J. Pharm. Sci. 76(2), p. 180-184. Various mono- and diacyl esters of ganciclovir are disclosed with their methods of preparation. However, L-valyl ester of ganciclovir and their process of preparation are not mentioned in this article.

European Patent Application 0 694 547 A discloses an antiviral compound with improved oral absorption and low toxicity which is a L-monovaline ester derived from 2-(2-amino-1,6-dihydro-6-oxo-purin-9-yl)methoxy-1,3-propanediol and its pharmaceutically acceptable salts.

The process typically described in the said European Patent Application is:
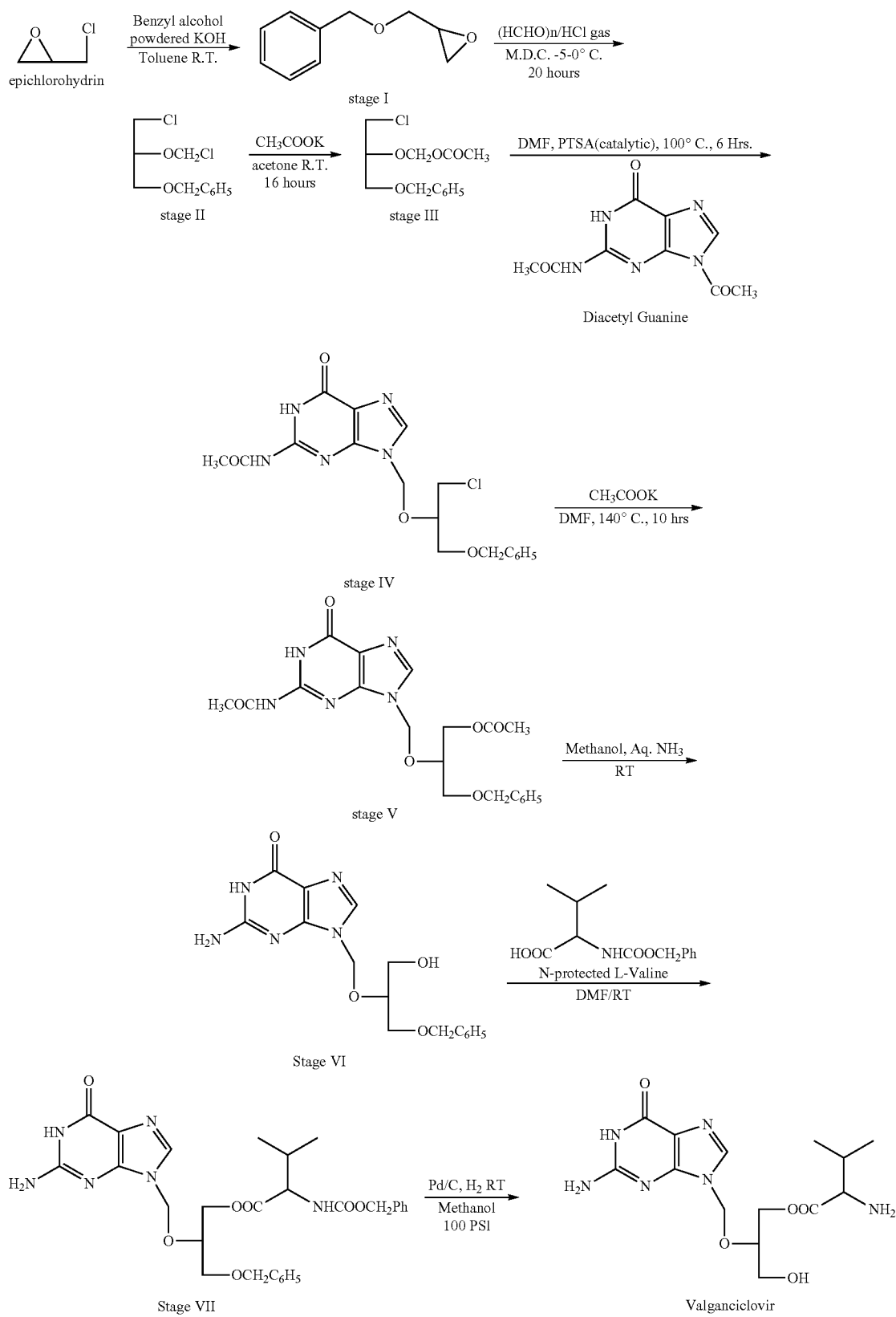

U.S. Pat. Nos. 5,700,936, 5,756,736, 5,840,890, 5,856, 481, 5,840,891, 6,083,953, 6,103,901, 6,040,446, 6,215,017, 6,218,568, and US patent application 2002/042424 provide processes for preparation of mono L-valyl ester of ganciclovir of formula I, wherein Z is hydrogen or an amino protecting group or pharmaceutically acceptable salt thereof which involves protection of either of the two hydroxy groups of optionally amino protected ganciclovir and treating the monohydroxy protected ganciclovir of formula II, wherein $P_1$ is an amino protecting group and $P_2$ is hydroxy protecting group with protected L valine of formula III, wherein Z is amino protecting group, to get protected monovalyl ester of ganciclovir of formula IV.

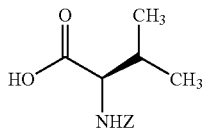

Formula III

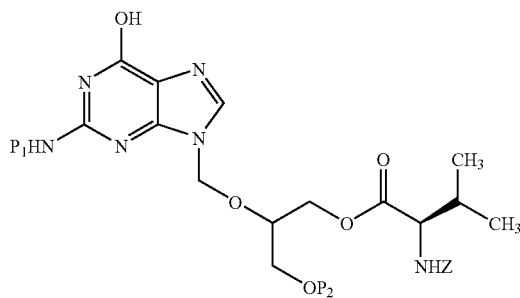

Formula IV

The compound is deprotected to get valganciclovir of formula I or pharmaceutically acceptable salt thereof in crystalline form.

Thus, the above mentioned prior art processes involve various protected and partially protected ganciclovir derivatives as intermediates. For example, U.S. Pat. Nos. 5,700,936, 5,756,736, 5,840,890, 5,856,481 involve divalinate N,O-bistrityl, monocarboxylate-monovalinate, bis(L-valinate) intermediates. While U.S. Pat. Nos. 6,040,446, 6,215,017 & 6218568 involve persilyl guanine or glycerol derivatives as intermediates.

These various above-mentioned intermediates are then subsequently deprotected and converted to valganciclovir of Formula I or pharmaceutically acceptable salt thereof in crystalline form.

Again WO97/27197 discloses a process explained in the scheme:

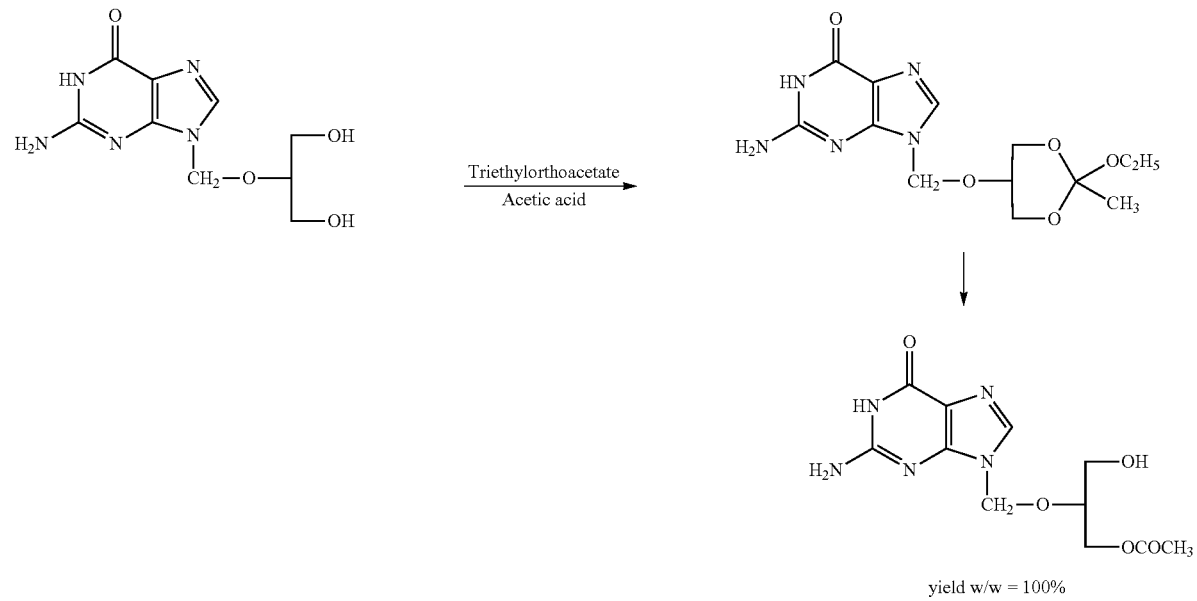

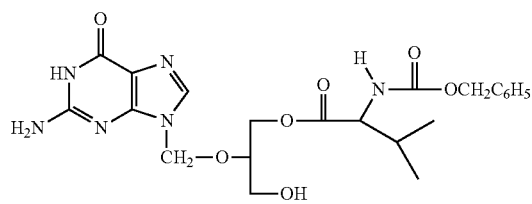

Yield w/w = 77%
HPLC purity = 65-70%

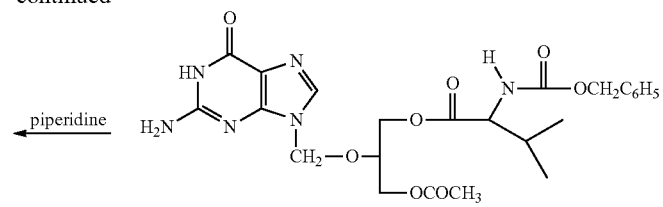

Yield w/w = 150%
HPLC purity = 80%

↓ 10% Pd/C

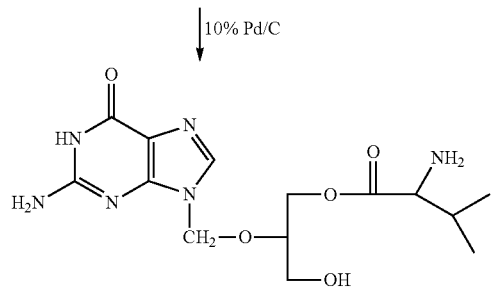

Valganciclovir
Yield w/w = 60%
HPLC purity = 98%

Patent application WO2005/092891 details a process for the preparation of the optically pure form of valganciclovir or pharmaceutically acceptable salts thereof by using a solvent or a solvent system characterized in that ganciclovir is soluble in it. Examples of such solvents disclosed include dimethylsulphoxide and sulpholane.

BRIEF DESCRIPTION OF THE PRESENT INVENTION

The present invention discloses an improved process for the preparation of mono-L-valine ganciclovir, in which protection or deprotection of hydroxy groups of the ganciclovir moiety, is not required.

A further object of this invention is to provide a scheme that does not use ganciclovir for synthesis of valganciclovir.

The process of the present invention involves the selective hydrolysis of 2(2-acetamido,1,6-dihydro-6-oxo-purine-9-yl)-methoxy-1,3-propane diol diactate(triacetyl ganciclovir) to 2-(2-amino-1,6-dihydro-6-oxo-purine-9-yl)-methoxy-3-acetoxy-1-propanol (mono acetyl ganciciovir). Selective hydrolysis in the context of this invention means the content of mono acetyl ganciclovir in the hydrolysed product is greater than 50%.

This invention provides a process for preparing the compound of formula (I) and pharmaceutically acceptable salts thereof, which is named 2-(2-amino-1,6-dihydro-6-oxo-purin-9-yl)methoxy-3-hydroxy-1-propyl-L-valinate or mono-L-valine ganciclovir.

According to this invention there is provided a process for the preparation of valganciclovir or a pharmaceutically acceptable salt thereof, with triacetyl ganciclovir as a starting material, said process comprising the following steps:

a) selective hydrolysis of triacetyl ganciclovir of Formula V, with a reagent, to monoacetyl ganciclovir, optionally in the presence of a first solvent;

Formula V

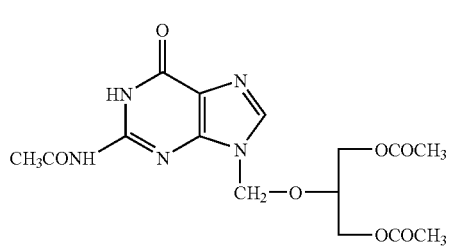

b) esterification of monoacetyl ganciclovir obtained from step (a), with CBZ Valine, with a coupling agent and a second solvent to give a compound of Formula VI

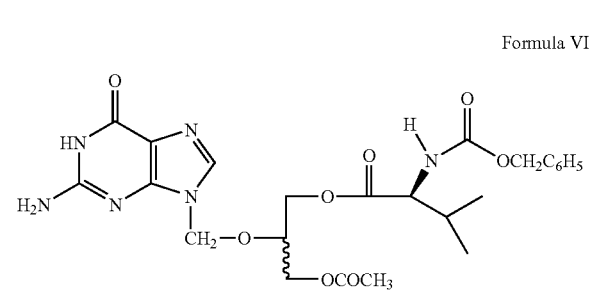

formula VI;

c) hydrolysis under basic conditions of compound of Formula VI; using an amine to give N-Benzyloxy carbonyl valganciclovir, and d) hydrogenolysis in the presence of a catalyst, under acidic conditions of N-Benzyloxy carbonyl valganciclovir to give valganciclovir.

Preferably, the reagent used in step (a) & (c) is at least one amine selected from a group of amines consisting of piperidine, piperazine, N-methyl piperazine, ethylene diamine, ethanol amine, N-methylcyclopentylamine, N-ethylphenylamine, diphenylamine, pyridine, triethylamine, diethyl amine, dibutyl amine, diisopropyl ethyl amine, morpholine and other cyclic amines.

Typically, the first solvent is at least one solvent selected from a group of solvents consisting of amines, alcohols, water, esters, nitriles, ethers and polar aprotic solvents.

Typically, the coupling agent is dicyclohexyl carbodiimide and the second solvent is a mixture of dichloromethane and DMF.

Alternatively, the coupling agent is CDI and the second solvent is DMF or mixture of dichloromethane & DMF.

Typically, the basic conditions for hydrolysis are created using an amine.

Typically, the catalyst is selected from a group of catalysts consisting of palladium on carbon, platinum and palladium hydroxide on carbon.

Typically, acidic conditions are created with at least one acid selected from a group of acids consisting of hydrochloric acid, sulphuric acid, acetic acid, ascorbic acid and citric acid.

This process involves selective hydrolysis of triacetyl ganciclovir to monoacetyl ganciclovir. Triacetyl ganciclovir is a relatively cheaper starting material as compared to ganciclovir, and may be prepared by processes known in the art, for example according to U.S. Pat. No. 5,583,225 & U.S. Pat. No. 5,821,367.

Selective hydrolysis is carried out typically using piperidine or piperazine at a temperature range of 25 to 80° C.

Monoacetyl ganciclovir is subsequently esterified with activated form of valine with a coupling agent typically using dicyclohexyl carbodiimide with a mixture of dichloromethane and DMF.

The monocarboxylate ester from the above step is hydrolysed under basic conditions typically using piperidine at 25 to 30° C.

N-Benzyloxy carbonyl Valganciclovir is subjected to hydrogenolysis in presence of a catalyst typically using palladium on carbon under acidic conditions typically using hydrochloric acid to give valganciclovir.

DETAILED DESCRIPTION

Synthetic Reaction Parameters

The reaction a step a) may be carried out at temperatures from 10 to 100° C., preferably from 30 to 80° C., e.g. from 50 to 80° C. for 2 to 80 hours.

The reaction of step b) may be carried out at temperatures from 30 to 100° C., preferably from 40 to 90° C., e.g. from 50 to 70° C. Preferably, the reaction of step b) may be carried out in the presence of dicyclohexyl carbodiimide and a suitable solvent preferably, a mixture of dichloromethane and DMF.

The reaction of step c) may be carried out may be carried out at temperatures from 10 to 100° C., preferably from 25 to 80° C., e.g. from 25 to 40° C.

The reaction of step d) may be carried out at temperatures from 10 to 60° C., preferably from 20 to 60° C., e.g. from 25 to 35° C. for 4 to 5 hrs.

Catalyst of step d) can be palladium on carbon, or palladium hydroxide on carbon or platinum under acidic conditions.

The isolation and purification procedures described herein can be effected, if desired, by any suitable separation or purification procedure such as, for example, filtration, extraction, crystallization, column chromatography, thin-layer chromatography or preparative chromatography, or a combination of these procedures. Specific illustrations of suitable separation and isolation procedures can be had by reference to the examples herein below. However, other equivalent separation or isolation procedures can, of course, also be used.

While considerable emphasis has been placed herein on the specific steps of the preferred process, it will be appreciated that many steps can be made and that many changes can be made in the preferred steps without departing from the principles of the invention. These and other changes in the preferred steps of the invention will be apparent to those skilled in the art from the disclosure herein, whereby it is to be distinctly understood that the foregoing descriptive matter is to be interpreted merely as illustrative of the invention and not as a limitation.

Details of the Synthetic Processes

The process of the present invention is depicted in the Reaction Sequence shown below in Scheme I:

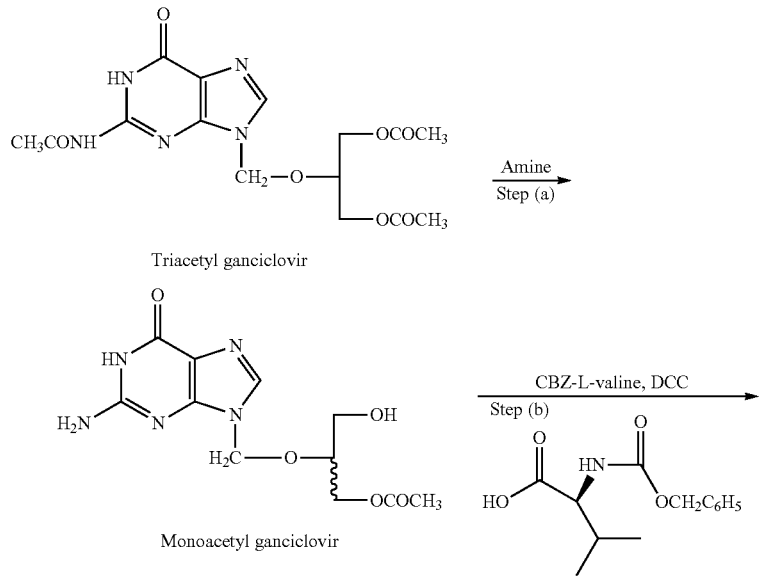

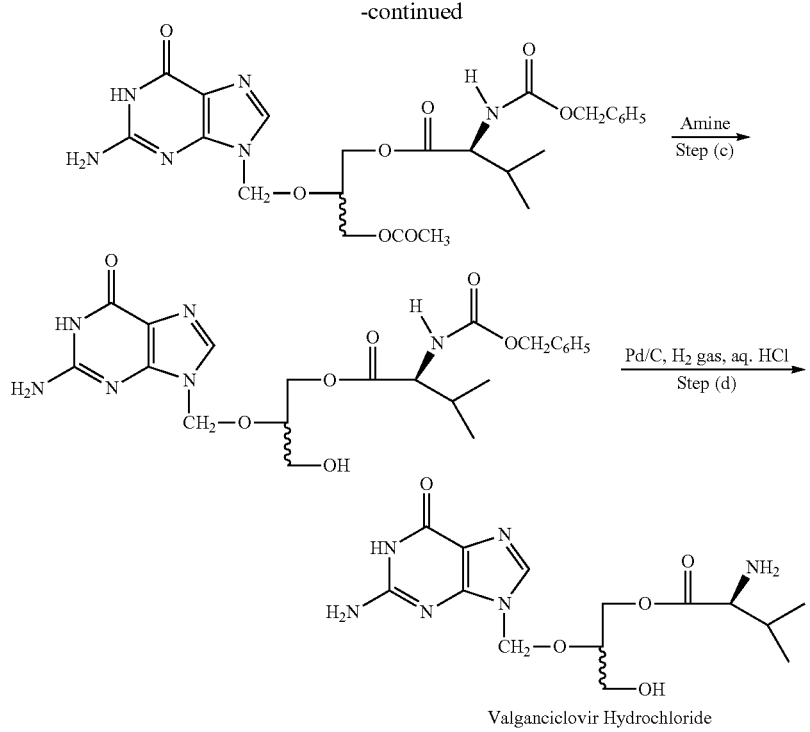

Stepwise Details
Step (a)
Selective Hydrolysis

Triacetyl ganciclovir is hydrolysed to monoacetyl ganciclovir with a reagent typically an amine preferably by using 2 to 10 vol Piperdine and or 2 to 10 vol of Dimethyl Acetamide in temp. range of 30 to 80° C. for 2 to 80 hours to yield 70% of monoacetyl ganciclovir.

The reaction is carried out optionally in the presence of a solvent selected from a group of solvents consisting of alcohols, esters, nitriles, water, ethers, polar aprotic solvent and mixtures thereof. Other suitable amines may include piperidine, piperazine, N-methyl piperazine, ethylene diamine, ethanol amine N-methylcyclopentylamine, N-ethylphenylamine, diphenylamine, pyridine, triethylamine, diethyl amine, dibutyl amine, diisopropyl ethyl amine, morpholine and other cyclic amines.
Step (b)
Esterification Reaction of monoacetyl ganciclovir with CBZ-L-valine, is carried out with a coupling agent typically using dicyclohexyl carbodiimide or carbonyl diimidazole as a coupling agent in a mixture of dichlomethane and DMF to get CBZ Valine condensed product.
Step (c)
Hydrolysis Product from step (2) is hydrolysed under basic conditions using an amine, typically using piperidine at 25 to 30° C. to give N-Benzyloxy carbonyl Valganciclovir
Step (d)
Hydrogenolysis N-Benzyloxy carbonyl Valganciclovir is hydrogenated under acidic conditions, in the presence of catalysts such as palladium on carbon, palladium hydroxide on carbon and platinum with bubbling hydrogen gas at 25-30° C. for 4-5 hrs, optionally at a hydrogen pressure below 50 psi. N-Benzyloxy carbonyl group which is attached to the valine component of the molecule is removed in this step.

The following specific examples are presented to illustrate the preferred mode of carrying out the process of the present invention. The examples are not limited to the particular embodiments illustrated herein but include the permutations, which are obvious as set forth in the forgoing description.

EXAMPLES

Example 1

Step (a)

Preparation of 2-(2-amino-1,6-dihydro-6-oxo-purine-9-yl)-methoxy-3-acetoxy-1-propanol 2(2-acetamido,1,6-dihydro-6-oxo-purine-9-yl)-methoxy-1,3-propane-diol diactate (Triacetyl ganciclovir) (100 gms) was stirred in N,N-dimethyl acetamide (200 ml) and piperidine (200 ml). Reaction mass was heated at 50-55° C. for 48 hrs. After cooling this reaction mass to 25° C., hexane (1 ltr) was added and stirred for 30 min and allowed to settle. Upper hexane layer was removed and acetone (20 ml) was added and stirred further. Hexane (500 ml) was added while stirring and resulting solid was filtered and dried under vacuum at 50° C. to get 70 gms of titled compound.

Step (b)

Preparation of 2-(2-amino-1,6-dihydro-6-oxo-purine-9-yl)-methoxy-3-acetoxy-1-propyl-N-(benzyloxycarbonyl)-L-valinate N-CBZ-L-valine (170 gms), dicyclohexyl carbodiimide (130 gms) were stirred in dichloromethane (2 liters). Product from step (a) (70 gms) was added to the reaction mass and stirred for 3-4 hours.

Dimethyl formamide (140 ml) and dimethyl amino pyridine (0.82 gms) were added to the reaction mass and stirred at 25° C. for 12 hours. Reaction mass was filtered, typically using a diatomaceous earth filter (for example: Hyflo). Clear filtrate was concentrated under vacuum to remove DMF. Oily residue was dissolved in isopropyl alcohol (180 ml) and hexane (700 ml) was added and stirred for 30 minutes and allowed to settle. The upper hexane layer was decanted. Oily layer was further stirred in a mixture of isopropyl alcohol and hexane for 1 hour, resulting solid was filtered and washed with hexane and dried under vacuum at 50° C. to get 34 gms of titled compound.

Step (c) Preparation of 2-(2-amino-1,6-dihydro-6-oxo-purine-9-yl)-methoxy-3-hydroxy-1-propyl-N-(benzyloxycarbonyl)-L-valinate Step (b) product (34 gms) and piperidine (68 ml) were stirred at 25° C. for 48 hours. After completion of reaction, Isopropyl alcohol (136 ml) was added, stirred and further hexane (340 ml) was added and stirred for 15 min and allowed to settle. Hexane layer was decanted and oil was further stirred in a mixture of isopropyl alcohol and hexane for 1 hour. The resulting solid was filtered and washed with hexane and dried under vacuum at 50° C. to get 29 gms of the titled compound purified using conventional acid base purification method.

Step (d)

Preparation of 2-(2-amino-1,6-dihydro-6-oxo-purine-9-yl)-methoxy-3-hydroxy-1-propyl-L-valinate hydrochloride Product from Step (c) (29 gms) was added to mixture of ethyl alcohol (700 ml) and water 170 ml. 10% palladium on carbon (5.8 gms) was added followed by conc. HCL (5.8 ml). Reaction mass was stirred at 25-30° C. Hydrogen gas was bubbled through the reaction mass for 12 to 20 hours. After completion of reaction, the reaction mass was filtered typically using a diatomaceous earth filter (for example: Hyflo) filtrate was concentrated to residue. The residue was dissolved in 50 ml water under stirring and further 600 ml of isopropyl alcohol was charged slowly in 2 hrs at 25-30° C. The resulting suspension was stirred at 25-30° C. for 30 minutes, and was filtered and washed with 50 ml isopropyl alcohol. The solid was dried under vacuum at 50° C. to get 20 gms of 2-(2-amino-1,6-dihydro-6-oxo-purine-9-yl)-methoxy-3-acetoxy-1-propyl-N-(benzyloxycarbonyl)-L-valinate hydrochloride (Valganciclovir Hydrochloride).

Example 2

Preparation of 2-(2-amino-1,6-dihydro-6-oxo-purine-9-yl)-methoxy-3-acetoxy-1-propanol Triacetyl ganciclovir (50 gms) was stirred in N,N-dimethyl acetamide (200 ml) and piperidine (200 ml). Reaction mass was heated at 75° C. for 3 hrs. The reaction mass was cooled to 25° C. and hexane (1 ltr.) was added and stirred for 30 min and allowed to settle. Upper hexane layer was removed and acetone (20 ml) was added and stirred further. Hexane (500 ml) was added while stirring and resulting solid was filtered and dried under vacuum at 50° C. to get 40 gms of titled compound, which was then converted to valganciclovir following the reaction conditions as mentioned in step-b to step-d of Example 1.

Example 3

Triacetyl ganciclovir (100 gms) was stirred with piperidine (400 ml). Reaction mass was heated at 50-55° C. for 48 hrs.

The reaction mass was cooled to 25° C. and heptane (2 ltr.) was added and stirred for 30 min and allowed to settle. Upper heptane layer was removed and Isopropyl alcohol (50 ml) was added and stirred further. Heptane (1 hr.) was added while stirring and resulting solid was filtered and dried under vacuum at 50° C. to get 80 gms of 2-(2-amino-1,6-dihydro-6-oxo-purine-9-yl)-methoxy-3-acetoxy-1 propanol, which was the converted to valganciclovir following the reaction conditions as mentioned in step-b to step-d of Example 1.

Example 4

Triacetyl ganciclovir (100 gms) was stirred with N,N-dimethyl-acetamide (400 ml) and piperazine (100 gins). Reaction mass was heated at 70-75° C. for 48 hrs. The reaction mass was cooled to 25° C. and hexane (2 ltr.) was added and stirred for 30 min and allowed to settle. Upper hexane layer was removed and acetone (50 ml) was added and stirred further. Hexane (1 hr.) was added while stirring and resulting solid was filtered and dried under vacuum at 50° C. to get 75 gms of 2-(2-amino-1,6-dihydro-6-oxo-purine-9-yl)-methoxy-3-acetoxy-1-propanol, which was then converted to valganciclovir following the reaction conditions as mentioned in step-b to step-d of Example 1.

Example 5

Triacetyl ganciclovir (100 gms) was stirred with N,N-dimethyl acetamide (400 ml) and morpholine (100 ml). Reaction mass was heated at 70-75° C. for 48 hrs. The reaction mass was cooled to 25° C. and hexane (2 ltr.) was added and stirred for 30 min and allowed to settle. Upper hexane layer was removed and acetone (40 ml) was added and stirred further. Hexane (1 ltr.) was added while stirring and resulting solid was filtered and dried under vacuum at 50° C. to get 70 gms of 2-(2-amino-1,6-dihydro-6-oxo-purine-9-yl)-methoxy-3-acetoxy-1-propanol, which was then converted to valganciclovir following the reaction conditions as mentioned in step-b to step-d of Example 1.

Valganciclovir is used for the treatment for an AIDS-related complication called CMV-retinitis. This is caused by a virus called CMV (Cytomegalovirus), which infects the eye. If left untreated, CMV retinitis can cause people with HIV/AIDS (PHAs) to go blind.

Valganciclovir is used for prophylaxis of CMV infection and disease in high-risk solid organ transplant recipients for example, in heart, renal and bone marrow transplants.

Valganciclovir is also useful for the treatment of certain carcinomas or lymphomas caused by, or related to, viral infections, such as nasopharyngeal cancer, immunoblastic lymphoma, Burkitt's lymphoma, and hairy leukoplakia.

The invention claimed is:

1. A process for the preparation of valganciclovir or a pharmaceutically acceptable salt thereof, with triacetyl ganciclovir (V) as a starting material, said process comprising the following steps:
    a) selective hydrolysis of triacetyl ganciclovir of Formula V to monoacetyl ganciclovir of Formula Va, optionally in the presence of a first solvent, wherein the selective hydrolysis comprises reacting triacetyl ganciclovir of Formula V with an amine;

Formula V

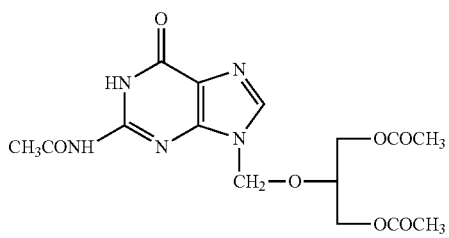

Formula Va

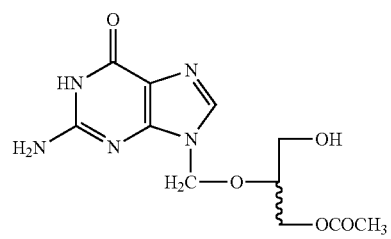

b) reacting monoacetyl ganciclovir obtained from step (a), with CBZ Valine, with a coupling agent and a second solvent, to give compound of Formula VI;

Formula VI

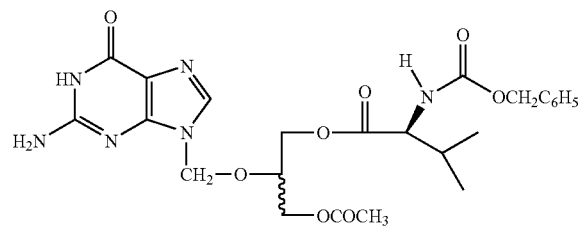

c) hydrolysis under basic conditions of compound of Formula VI; using an amine to give N-Benzyloxycarbonyl valganciclovir, d) hydrogenolysis in the presence of a catalyst, under acidic conditions of N-Benzyloxycarbonyl valganciclovir to give valganciclovir, and e) optionally converting valganciclovir to a pharmaceutically acceptable salt thereof.

2. A process as claimed in claim 1, wherein the first solvent is at least one solvent selected from a group of solvents consisting of amines, alcohols, esters, water, nitriles, ethers and polar aprotic solvents.

3. A process as claimed in claim 1, wherein the amine used in step (a) and step (c) is at least one amine selected from a group consisting of, piperidine, piperazine, N-methyl piperazine, ethylene diamine, ethanol amine, N-methylcyclopentylamine, N-ethylphenylamine, diphenylamine, pyridine, triethylamine, diethyl amine, dibutyl amine, diisopropyl ethyl amine and morpholine.

4. A process as claimed in claim 1, wherein the coupling agent is dicyclohexyl carbodiimide and the second solvent is a mixture of dichloromethane and DMF.

5. A process as claimed in claim 1, wherein the coupling agent is N,N-carbonyl diimidazole and the second solvent is a mixture of dichloromethane and DMF.

6. A process as claimed in claim 1, wherein the catalyst is selected from a group of catalysts consisting of palladium on carbon, platinum and palladium hydroxide on carbon.

7. A process as claimed in claim 1, wherein acidic conditions are created with at least one acid selected from a group of acids consisting of hydrochloric acid, sulphuric acid, acetic acid, ascorbic acid and citric acid.

\* \* \* \* \*